United States Patent
Johnson

[19]

[11] Patent Number: 5,954,054

[45] Date of Patent: Sep. 21, 1999

[54] MALE CONDOM

[76] Inventor: Joseph T. Johnson, 8028 Regent Park La., Charlotte, N.C. 28210

[21] Appl. No.: 09/123,656

[22] Filed: Jul. 28, 1998

Related U.S. Application Data

[63] Continuation-in-part of application No. 08/379,021, Jan. 27, 1995, Pat. No. 5,785,052.

[51] Int. Cl.$^6$ ....................................................... A61F 6/04
[52] U.S. Cl. .......................................... 128/844; 128/918
[58] Field of Search .................................... 128/842, 844, 128/918; 604/347–353

[56] References Cited

U.S. PATENT DOCUMENTS

| | | | |
|---|---|---|---|
| 4,919,149 | 4/1990 | Stang | 128/844 |
| 5,016,649 | 5/1991 | Johnson | 128/859 |
| 5,314,447 | 5/1994 | Papurt | 128/842 |
| 5,370,130 | 12/1994 | Hess | 128/844 |
| 5,469,863 | 11/1995 | Shah | 128/844 |
| 5,785,052 | 7/1998 | Johnson . | |

*Primary Examiner*—Michael A. Brown
*Attorney, Agent, or Firm*—Christopher C. Dremann PC; Christopher C. Dremann

[57] ABSTRACT

A male condom for preventing unwanted pregnancy and protecting against communicable diseases transmitted by the exchange of bodily fluids includes a flaccid pouch made of a thin disposable film of fluid impervious material and a flaccid pouch harness. The flaccid pouch consists of an elongate, hollow, generally cylindrical body defining a longitudinal axis and having a first end and a second end. The first end is typically open, but the male condom may be provided with a thin breakable-seal entrance shield to temporarily close the first end. The male condom further includes at least one longitudinally extending, thin breakable-seal web formed on the exterior surface of the body and defining a hollow cavity for storing a liquid or gel lubricant and/or spermicide. The flaccid pouch harness includes an annular retaining ring made of a thicker disposable film of fluid impervious material and attached to the flaccid pouch adjacent the first end of the body. Preferably, the flaccid pouch harness further includes at least one radially extending application handle formed in a closed loop and depending generally outwardly from the exterior surface of the retaining ring. Preferably, the flaccid pouch harness also includes at least one longitudinally extending retaining band depending generally rearwardly from the retaining ring.

19 Claims, 4 Drawing Sheets

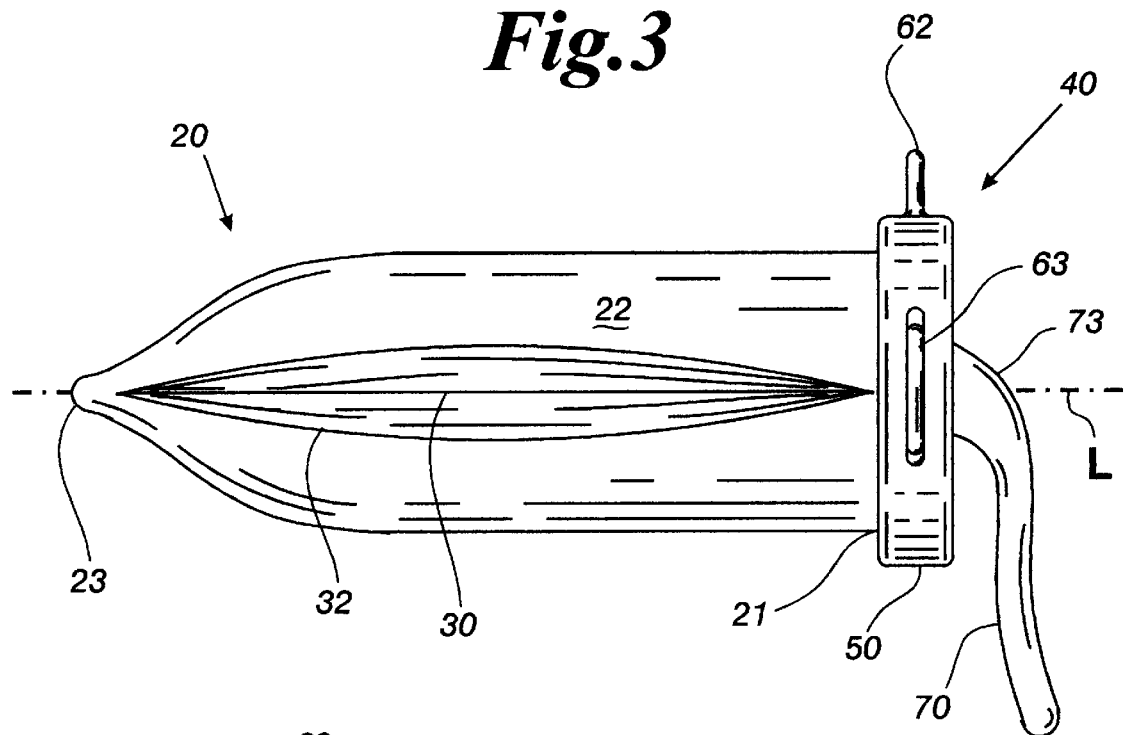
*Fig.3*
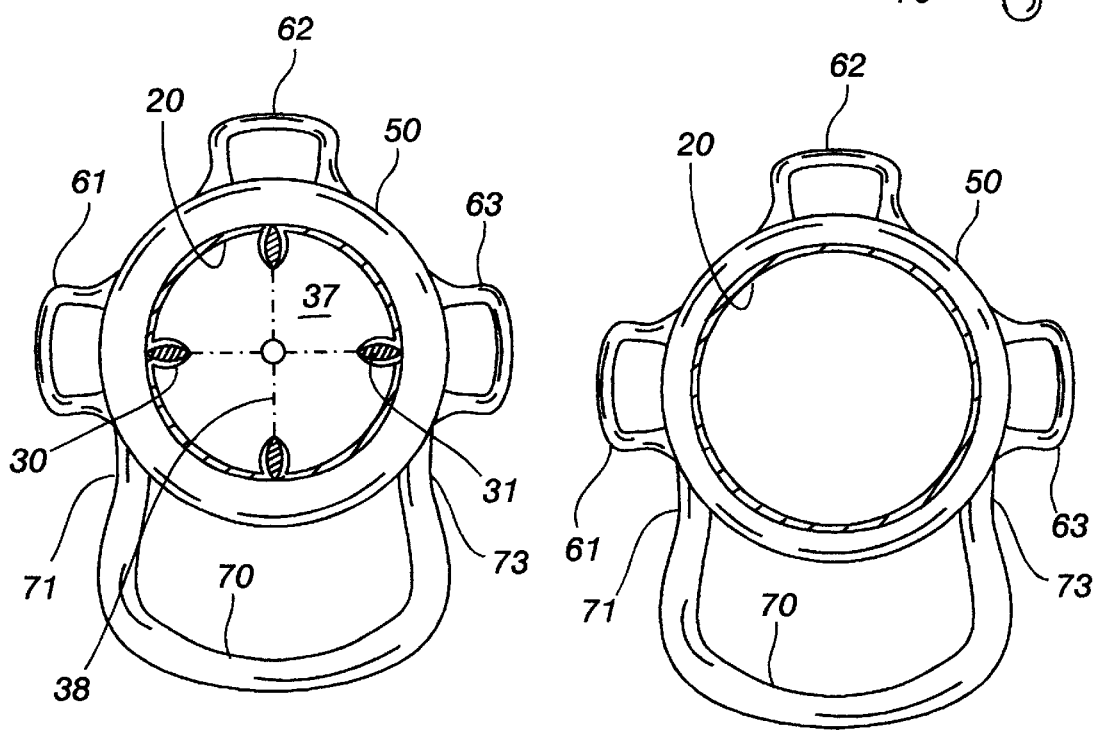
*Fig.4*  *Fig.5*

MALE CONDOM

CROSS REFERENCE TO RELATED APPLICATIONS

This application is a continuation-in-part of U.S. Pat. application Ser. No. 08/379,021, filed Jan. 27, 1995, which issued Jul. 28, 1998, as U.S. Pat. No. 5,785,052.

FIELD OF THE INVENTION

The invention relates to a male condom which is designed and constructed to effectively prevent unwanted pregnancy and to protect the wearer against communicable diseases, including viral diseases such as Human Immunodeficiency Virus (HIV) which has been known to lead to the development of Acquired Immunodeficiency Syndrome (AIDS). The wearer of the male condom is also effectively protected against other Sexually Transmitted Diseases (STDs) such as herpes, syphilis and gonorrhea.

BACKGROUND OF THE INVENTION

Sexual partners have long been mindful of unwanted pregnancy. Meanwhile, the public at large has become increasingly fearful of contracting communicable diseases, such as HIV/AIDS and other STDs, from sexual activity. It is well known that pregnancy occurs when the male sperm comes into contact with the female egg. It is also well known that STDs can be transmitted by the exchange of bodily fluids. Accordingly, the most widespread means of contraception and protection against STDs to date has been the male condom. Until now, however, there has not been a male condom that is highly effective in preventing unwanted pregnancy and at the same time guarding against the aforementioned public health concerns.

Known male condoms are primarily of two types. The first type consists of a thin, elongate, cylindrical body made of a form-fitting, fluid impervious material, such as latex, polyurethane or natural or synthetic rubber, which is open at one end and closed at the other end. The second type consists of a relatively thin, elongate, cylindrical body made of a loose-fitting, fluid impervious material, such as sheepskin or soft leather, which is open at one end and closed at the other end. The condom is open at one end for insertion of the penis and is closed at the other end to maintain a fluid-tight barrier between the wearer's penis and the sex organ, typically the mouth, vagina or anus, of the wearer's partner. Ideally, the condom prevents male sperm and other bodily fluids from being exchanged during sexual activity. For one reason or another, however, the male condoms available today do not adequately prevent the exchange of bodily fluids during sexual activity, and thus do not adequately prevent unwanted pregnancy or the transmission of STDs.

The design and construction of the male condoms available today are not well adapted for their intended purpose. For example, the available male condoms are generally difficult to properly apply to the penis of the wearer, particularly for those who are inexperienced or who may be under the influence of alcohol or drugs. If improperly applied, the condom may not provide an effective fluid-tight barrier, or worse yet, may become loose during the sexual activity and rendered completely ineffective in preventing the exchange of bodily fluids. Even if properly applied to the penis of the wearer, known male condoms can be inadvertently removed during sexual activity if the condom is not securely retained on the wearer's penis. The likelihood that the condom will become loose or inadvertently removed is enhanced once the condom is subjected to the bodily fluids typically generated during sexual activity. Removal of the condom prior to completion of the sexual activity permits the bodily fluids of the wearer to come into contact with, and thus be exchanged with, the bodily fluids of the wearer's partner.

Another deficiency in the design and construction of known male condoms is that many do not include a spermicide of any kind. Those that do most often utilize a spermicide that is coated in the form of a dry film on the exterior surface of the condom. Others provide a separate spermicide to be mixed with a liquid or gel lubricant and applied on the exterior surface of the condom. Whether coated or mixed with a lubricant, the spermicide can be rubbed off as the condom is removed from its packaging or positioned on the wearer's penis. Further still, spermicides rapidly lose their effectiveness when exposed to the ambient atmosphere. Accordingly, the use of a male condom including a spermicide can be rendered ineffective unless the condom is used shortly after it is removed from its packaging, carefully positioned on the wearer's penis prior to the sexual activity and securely retained on the penis during the sexual activity.

It is therefore apparent that there exists a need for a male condom which effectively prevents unwanted pregnancy and protects against the transmission of STDs caused by the exchange of bodily fluids during sexual activity.

SUMMARY OF THE OBJECTS OF THE INVENTION

Accordingly, it is a principle object of the present invention to provide a male condom that is designed and constructed to be highly effective in preventing unwanted pregnancy as well as combating public health concerns, such as the transmission of STDs through the exchange of bodily fluids during sexual activity.

It is a further object of the present invention to provide a male condom that is easy to properly apply to the wearer's penis prior to sexual activity.

It is a further object of the present invention to provide a male condom that is securely retained on the wearer's penis during sexual activity.

It is a further object of the present invention to provide a male condom including a spermicide that is not exposed to the ambient atmosphere until the wearer's penis is inserted into the condom.

SUMMARY OF THE INVENTION

The invention is a male condom for preventing unwanted pregnancy and protecting against communicable diseases transmitted by the exchange of bodily fluids. The male condom includes a flaccid pouch, at least one longitudinally extending, thin breakable-seal web and a flaccid pouch harness. Preferably, the flaccid pouch is made of a thin disposable film of fluid impervious material which forms an elongate, hollow, generally cylindrical body defining a longitudinal axis and having a first end and a second end. The body is open at the first end and closed at the second end. The at least one breakable-seal web is formed on the exterior surface of the body of the flaccid pouch and defines a hollow cavity for storing a liquid or gel lubricant and/or spermicide. The flaccid pouch harness includes an annular retaining ring attached to the body adjacent the first end. Preferably, the retaining ring of the flaccid pouch harness is made of an elastic disposable film of fluid impervious material that is substantially thicker than the thin disposable film of the flaccid pouch.

In a preferred embodiment, the male condom further includes a thin breakable-seal entrance shield adjacent the first end of the body of the flaccid pouch. The entrance shield consists of a generally cylindrical, lateral flap having a plurality of radial perforations formed therein. The perforations hold the flap together so that the flaccid pouch is temporarily closed at the first end. A liquid or gel lubricant and/or spermicide may be stored within the cavity defined by the hollow flaccid pouch so that when the penis is inserted through the first end of the flaccid pouch, the thin breakable-seal entrance shield is broken and the lubricant and/or spermicide stored within the flaccid pouch is released. In this manner, the male condom is self-lubricating and does not require the use of a separate lubricant and/or spermicide.

In another preferred embodiment, the at least one breakable-seal web includes a plurality of circumferentially spaced, longitudinally extending, breakable-seal webs. The plurality of breakable-seal webs may include a pair of diametrically opposed, breakable-seal webs. Alternatively, the plurality of breakable-seal webs includes a first pair of diametrically opposed, breakable-seal webs and a second pair of diametrically opposed, breakable-seal webs positioned generally perpendicular to the first pair of breakable-seal webs.

In another preferred embodiment, the male condom further includes at least one application handle attached to the retaining ring of the flaccid pouch harness. In one embodiment, the at least one application handle extends radially and depends generally outwardly from the exterior surface of the retaining ring. In yet another embodiment, the at least one application handle extends longitudinally and depends generally rearwardly from the exterior surface of the retaining ring. The at least one application handle may have any convenient configuration, but preferably is formed in a closed loop.

The at least one application handle may include a plurality of circumferentially spaced application handles. For example, in one embodiment, the plurality of application handles includes a pair of diametrically opposed application handles. In an alternative embodiment, the plurality of application handles further includes a third application handle positioned medially between the pair of diametrically opposed application handles. In yet another embodiment, the plurality of application handles includes a first pair of diametrically opposed application handles and a second pair of diametrically opposed application handles positioned generally perpendicular to the first pair of diametrically opposed application handles.

In another preferred embodiment, the flaccid pouch harness of the male condom further includes at least one longitudinally extending retaining band attached to the retaining ring and depending generally rearwardly therefrom. Preferably, the at least one retaining band is made of an elastic disposable film of fluid impervious material that is slightly thicker than the thin disposable film of the flaccid pouch. The at least one retaining band may include a single retaining band having a first end and a second end attached to the retaining ring at diametrically opposed positions. The at least one retaining band may also be formed in a closed loop. The at least one retaining band may also include a pair of retaining bands, each of the retaining bands attached to the retaining ring on one side and to the other of the pair of retaining bands on the other side.

BRIEF DESCRIPTION OF THE DRAWINGS

In view of these and other objects which will more readily appear as the nature of the invention is better understood, the invention consists in the novel combination and arrangement of parts hereinafter more fully described, illustrated and claimed with reference being made to the attached drawings in which:

FIG. 3 is a side elevation view of the male condom of FIG. 2;

FIG. 4 is a sectional view of the male condom of FIG. 1 taken in the direction indicated by the line 4—4;

FIG. 5 is a sectional view of the male condom of FIG. 2 taken in the direction indicated by the line 5—5;

DETAILED DESCRIPTION OF THE PREFERRED EMBODIMENTS

Figure 1:
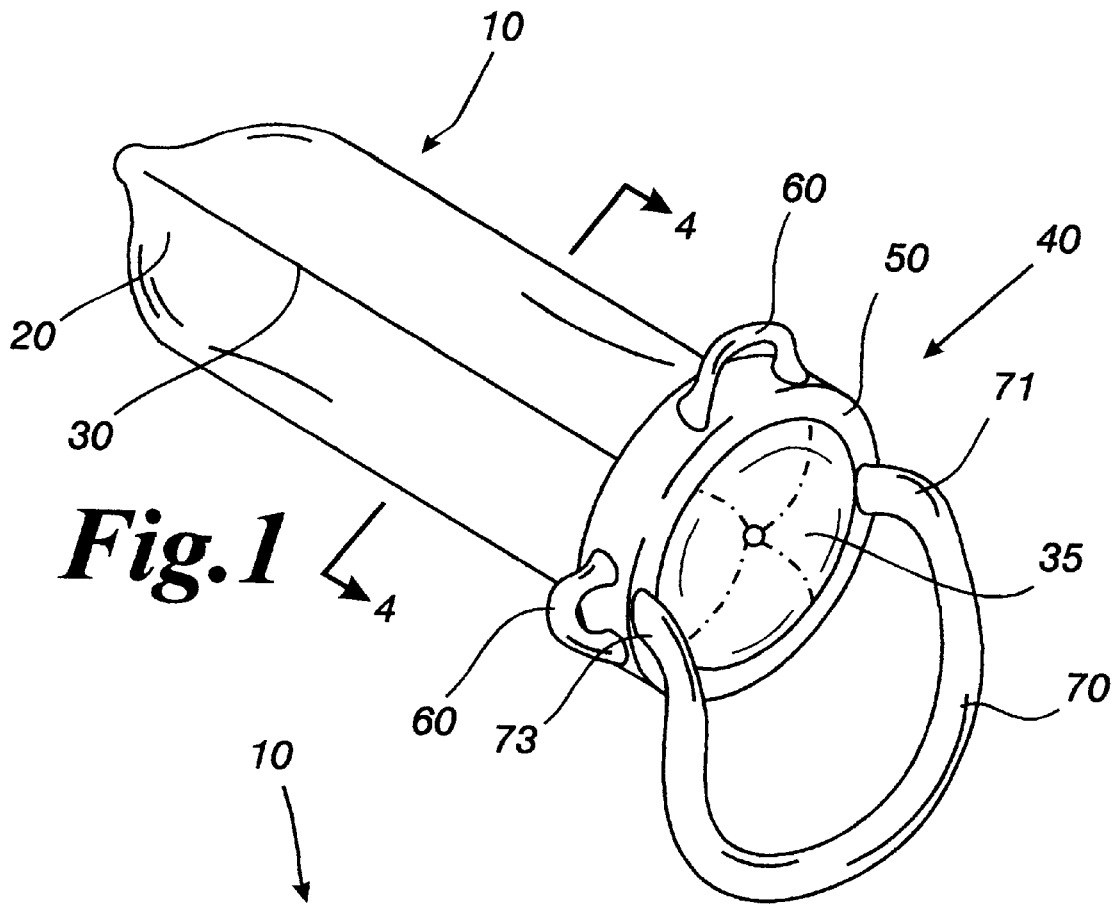
FIG. 1 is a perspective view of a preferred embodiment of a male condom according to the invention showing the thin breakable-seal web and the thin breakable-seal entrance shield unbroken.

A preferred embodiment of the present invention will be described more fully hereafter followed by a brief description of a number of alternative preferred embodiments. However, the invention should not be construed as being limited by the preferred embodiments described herein. Rather, it is intended that the invention be construed broadly to encompass any and all embodiments of a male condom having the disclosed features which is within the skill of an ordinary person in the art. In the description, like reference numerals designate like or corresponding parts throughout the several figures. It is to be also understood that such terms as "top", "bottom", "side", "front" and "rear" are used in the description for purposes of locating one element relative to another and are not to be construed as limiting terms. Finally, it should be understood that the illustrations provided in the figures are for the purpose of describing preferred embodiments of the invention, and thus are not intended to limit the invention in any manner.

Referring now to the accompanying figures, the invention is a male condom, indicated generally at 10, for preventing unwanted pregnancy and for protecting against the transmission of STDs, such as AIDS, through the exchange of bodily fluids, such as saliva, perspiration, sperm and blood, during sexual activity. In the broadest sense, the condom 10 comprises a flaccid pouch 20 and a flaccid pouch harness 40 comprising a retaining ring 50. In the majority of the preferred embodiments, the flaccid pouch harness 40 further comprises at least one application handle 60 and at least one retaining band 70, as will be described. In alternative embodiments, the location, number and configuration of the application handle(s) and the retaining band(s) varies.

As best shown in FIG. 3, the flaccid pouch 20 comprises an elongate, hollow, generally cylindrical body 22 defining a longitudinal axis L and having a first end 21 and a second end 23. The body 22 is open at the first end 21 and closed at the second end 23. Preferably, the second end 23 is also tapered to conform to the shape of the tip of the penis. The flaccid pouch 20 is made of a thin disposable film material. More preferably, the flaccid pouch 20 is made of a dipped or molded, uninterrupted liquid latex, liquid polyurethane or natural or synthetic rubber material that is impervious to fluids, and in particular is impervious to male sperm and to other bodily fluids that transmit liquid-born viruses, such as STDs.

Preferably, the male condom 10 further comprises at least one longitudinally extending, thin breakable-seal web 30 formed on the exterior surface of the body 22 of the flaccid pouch 20. When sealed, the web 30 defines a hollow cavity for storing a liquid or gel lubricant and/or spermicide 31 (FIG. 4). Preferably, the web 30 is created by forming creases or folds 32 in the body 22 of the flaccid pouch 20. The lubricant and/or spermicide 31 is then injected into the hollow cavity and the folds 32 are heat sealed or sealed with a light adhesive to temporarily store the lubricant and/or spermicide within the hollow cavity. When the penis of the wearer is inserted into the flaccid pouch 20, the thin breakable seal 32 of the web 30 is broken and the lubricant and/or spermicide 31 stored within the web 30 is released. Accordingly, the male condom 10 is self-lubricating and does not require the use of a separate lubricant and/or spermicide.

Preferably, the male condom 10 further comprises a thin breakable-seal entrance shield 35 (FIG. 1) adjacent the first end 21 of the body 22 of the flaccid pouch 20. The entrance shield comprises a generally cylindrical, lateral flap 37 having a plurality of radial perforations 38 formed therein. The perforations 38 hold the flap 37 together such that the flaccid pouch is temporarily closed at the first end 21. Thus, a liquid or gel lubricant and/or spermicide (not shown) may be stored within the cavity defined by the hollow flaccid pouch 20. When the penis is inserted through the first end 21 of the flaccid pouch 20, the thin breakable-seal entrance shield 35 is broken and the lubricant and/or spermicide stored within the flaccid pouch is released. Accordingly, the male condom 10 is self-lubricating and does not require the use of a separate lubricant and/or spermicide.

Figure 2:
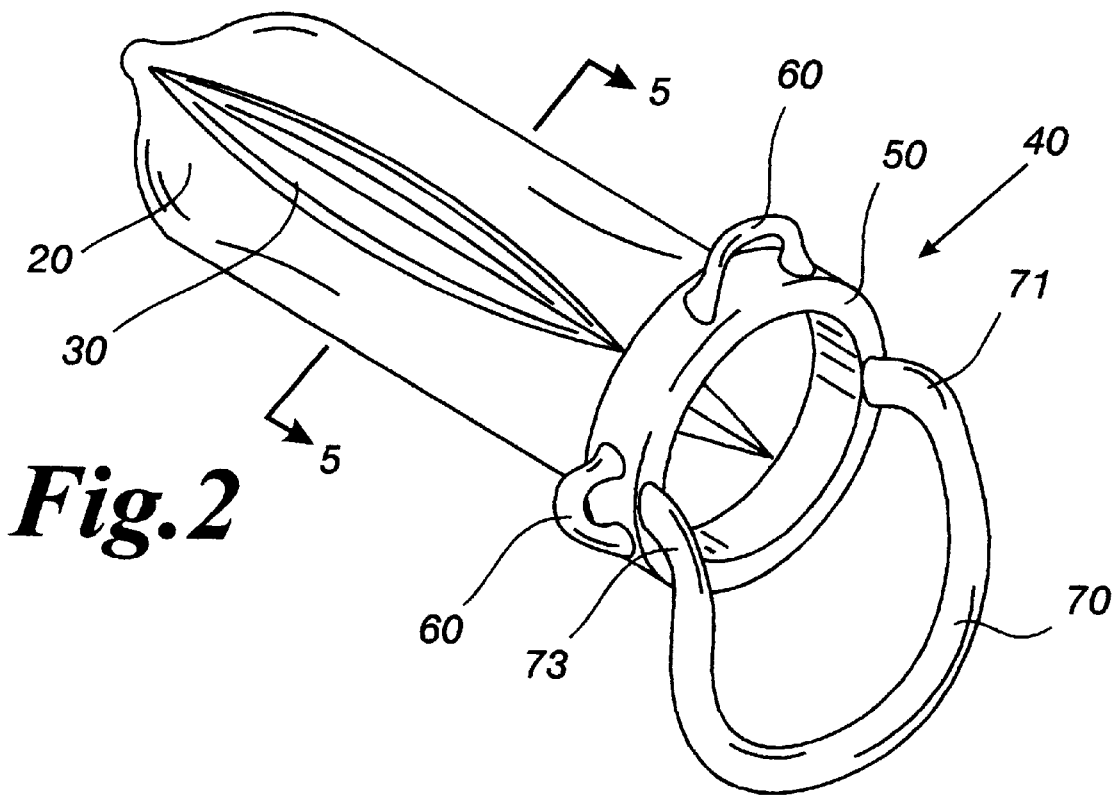
FIG. 2 is a perspective view of the male condom of FIG. 1 showing the thin breakable-seal web and the thin breakable-seal entrance shield broken.

FIG. 1 is a perspective view of a preferred embodiment of the male condom 10 showing the thin breakable-seal web 30 and the thin breakable-seal entrance shield 35 unbroken. FIG. 2 is a perspective view of the male condom 10 of FIG. 1 showing the thin breakable-seal web 30 and the thin breakable-seal entrance shield 35 broken. FIG. 4 is a sectional view of the male condom 10 of FIG. 1 taken in the direction indicated by the line 4—4, and FIG. 5 is a sectional view of the male condom 10 of FIG. 2 taken in the direction indicated by the line 5—5.

The flaccid pouch harness 40 comprises an annular retaining ring 50 attached to the cylindrical body 22 of the flaccid pouch 20 adjacent the first end 21. The retaining ring is made of an elastic disposable film material that is substantially thicker than the thin disposable film material of the flaccid pouch 20. More preferably, the retaining ring 50 is made of a dipped or molded, uninterrupted liquid latex, liquid polyurethane or natural or synthetic rubber material that is impervious to fluids, and in particular is impervious to male sperm and to other bodily fluids that transmit liquid-born viruses, such as STDs. The retaining ring 50 protects the relatively fragile flaccid pouch 20 against ripping and tearing while the male condom 10 is packaged prior to being used by the wearer. The elastic retaining ring 50 also applies a slight amount of pressure to the base of the penis to hold the male condom 10 on the penis more securely. Thus, it is less likely that the male condom 10 will be removed from the wearer during the course of the sexual activity.

The flaccid pouch harness 40 may further comprise at least one application handle 60 attached to the exterior surface of the retaining ring 50. The application handle 60 is provided to assist the wearer to apply the male condom 10 to the penis. Preferably, the flaccid pouch harness 40 comprises a plurality of application handles 60 wherein each application handle is formed in a closed loop to facilitate applying the male condom 10 to the penis. Most preferably, as best shown in FIGS. 3–5, the flaccid pouch harness 40 comprises three circumferentially spaced application handles 60 consisting of a pair of diametrically opposed handles 61, 63 and a third handle 62 positioned medially between the handles 61, 63. The pair of application handles 61, 63 prevent ripping or tearing the flaccid pouch 20 when applying the male condom 10 to the penis. The application handle 62 is used to release air that is trapped inside the flaccid pouch 20 by pulling upward on the handle. Accordingly, the flaccid pouch 20 is held more securely on the penis so that the male condom 10 is less likely to be removed from the wearer during the course of the sexual activity.

As shown in the preferred embodiment illustrated in FIGS. 1–5 and in the alternative embodiments illustrated in FIGS. 6–10, the application handles 61, 62, 63 may extend radially and depend generally outwardly from the retaining ring 50. As shown in the alternative embodiments illustrated in FIGS. 12–16 the flaccid pouch harness 40 may comprise a first pair of diametrically opposed application handles 64, 66 and a second pair of diametrically opposed application handles 65, 67 positioned generally perpendicular to the first pair of diametrically opposed application handles 64, 66. As shown in FIGS. 12–17, the application handles 64, 65, 66, 67 may also extend longitudinally and depend generally rearwardly from the retaining ring 50.

The flaccid pouch harness 40 may further comprise at least one longitudinally extending retaining band 70 attached to the retaining ring 50 and depending generally rearwardly therefrom. The retaining band 70 is made of an elastic disposable film material, such as latex, polyurethane or natural or synthetic rubber, that is slightly thicker than the thin disposable film material of the flaccid pouch 20. The retaining band 70 is positioned over the wearer's scrotum, indicated by the dashed lines in FIGS. 6–11 and 13–17, to securely retain the male condom 10 on the penis during the sexual activity. As shown, the retaining band 70 may be attached to the retaining ring 50 at different locations so that the retaining band contacts different pressure points on the wearer. In addition, a second retaining band 70' may be utilized to more securely retain the male condom 10 on the penis or to contact multiple pressure points on the wearer.

Figure 6:
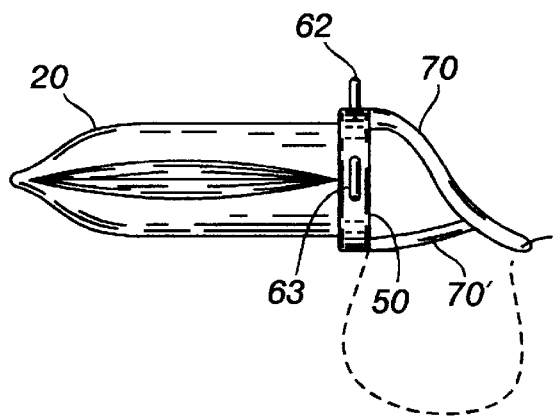
FIG. 6 is a side elevation view of an alternative embodiment of a male condom according to the invention.
Figure 9:
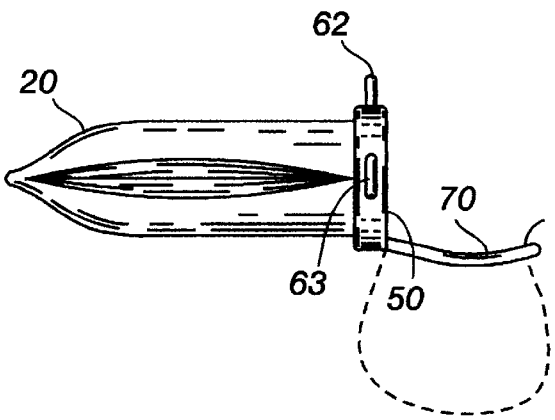
FIG. 9 is a side elevation view of an alternative embodiment of a male condom according to the invention.
Figure 7:
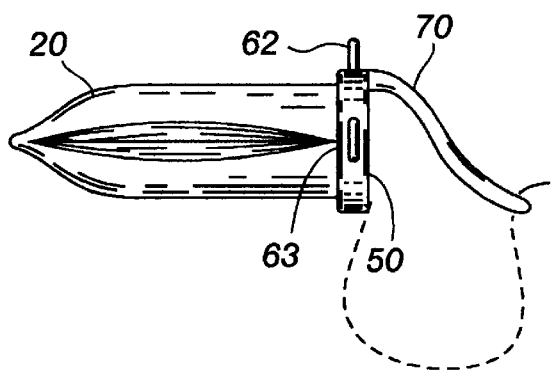
FIG. 7 is a side elevation view of an alternative embodiment of a male condom according to the invention.
Figure 10:
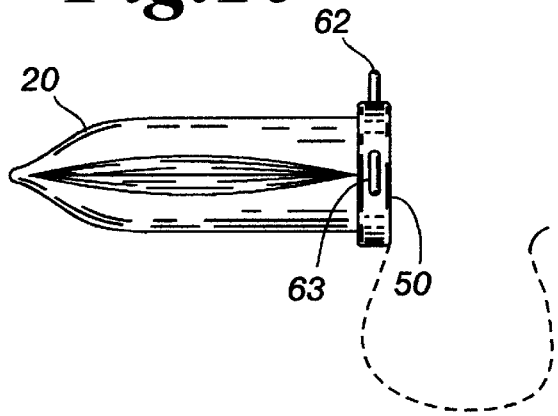
FIG. 10 is a side elevation view of an alternative embodiment of a male condom according to the invention.
Figure 8:
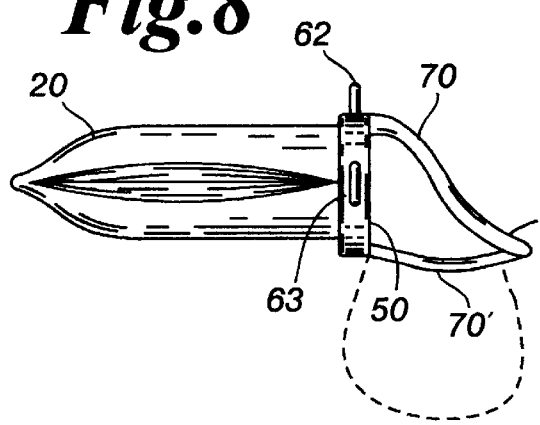
FIG. 8 is a side elevation view of an alternative embodiment of a male condom according to the invention.
Figure 11:
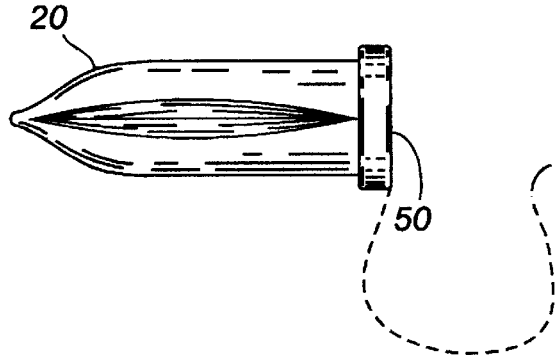
FIG. 11 is a side elevation view of an alternative embodiment of a male condom according to the invention.
Figure 12:
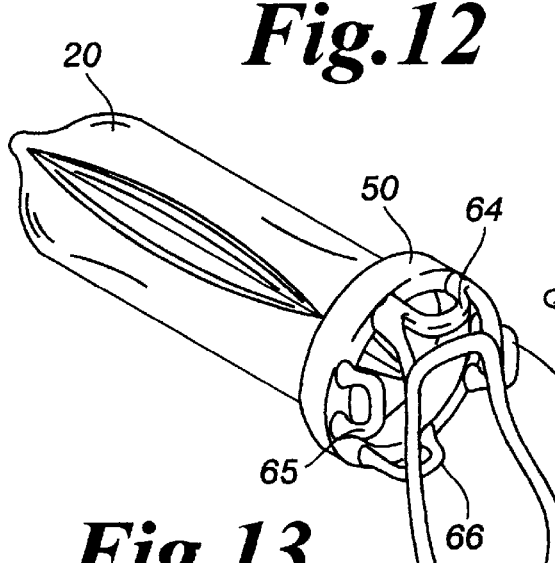
FIG. 12 is a perspective view of an alternative embodiment of a male condom according to the invention.
Figure 15:
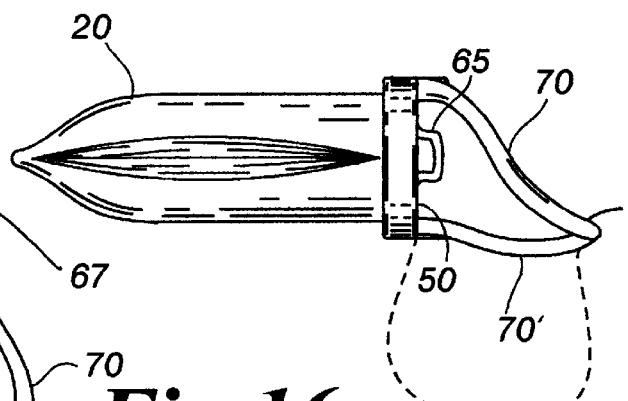
FIG. 15 is a side elevation view of an alternative embodiment of a male condom according to the invention.
Figure 13:
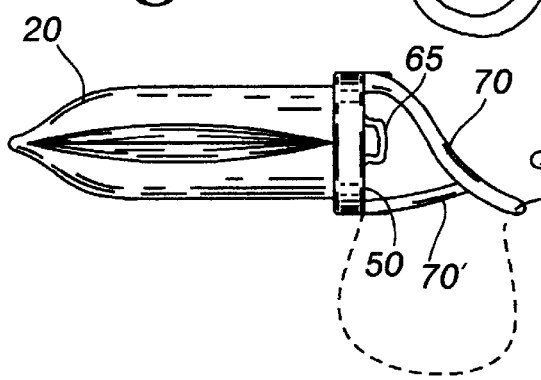
FIG. 13 is a side elevation view of an alternative embodiment of a male condom according to the invention.
Figure 16:
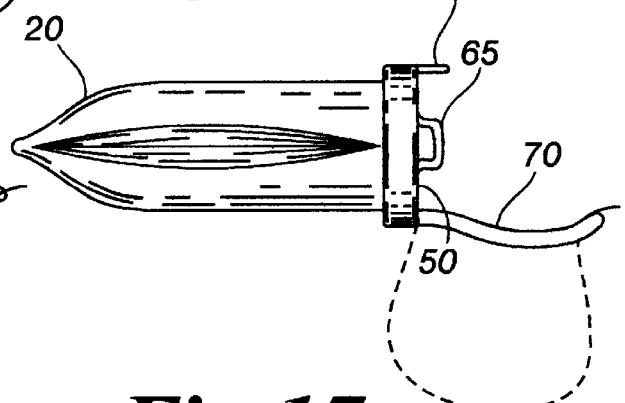
FIG. 16 is a side elevation view of an alternative embodiment of a male condom according to the invention.
Figure 14:
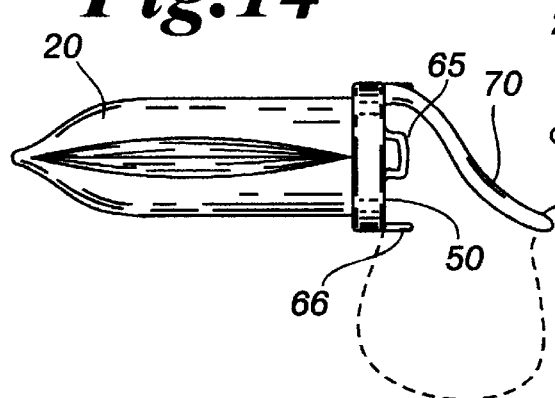
FIG. 14 is a side elevation view of an alternative embodiment of a male condom according to the invention.
Figure 17:
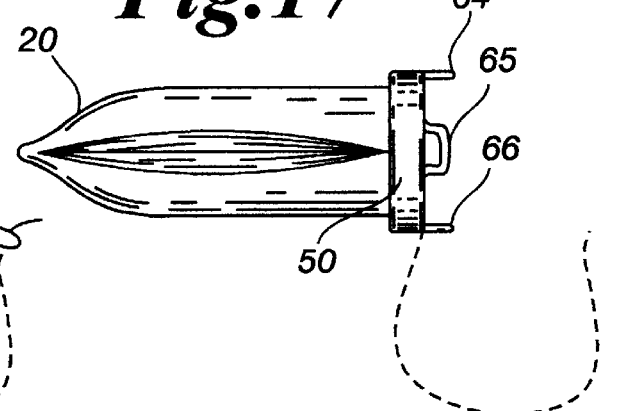
FIG. 17 is a side elevation view of an alternative embodiment of a male condom according to the invention.

In the preferred embodiment shown in FIGS. 1–5, the retaining band 70 has a first end 71 and a second end 73 attached to the retaining ring 50 at diametrically opposed positions. In the alternative embodiments shown in FIGS. 6–10 and FIGS. 12–17, each of the retaining bands 70 is formed in a closed loop and attached to the retaining ring 50 at a first position. The retaining band 70 may be attached to a second retaining band 70' at a second position opposite the first position (FIGS. 8 and 15), or at a third position located medially between the first position and the second position (FIGS. 6 and 13).

From the forgoing, it is readily apparent that the present invention provides a male condom that is designed and constructed to be highly effective in preventing unwanted pregnancy as well as combating public health concerns. It is further apparent that the present invention provides a male condom that is easy to properly apply to the wearer's penis prior to sexual activity, and that is securely retained on the wearer's penis during sexual activity. It is still further apparent that the present invention provides a male condom including a spermicide that is not exposed to the ambient atmosphere until the wearer's penis is inserted into the condom.

It is to be understood that the forgoing description and specific embodiments shown herein are merely illustrative of the best mode of the invention and the principals thereof, and that various modifications and additions may be made by those skilled in the art without departing unnecessarily from the spirit and scope of the invention, which is intended to be limited only by the scope of the appended claims.

That which is claimed is:

1. A male condom for preventing unwanted pregnancy and protecting against communicable diseases transmitted by the exchange of bodily fluids, said male condom comprising
   a flaccid pouch comprising an elongate, hollow, generally cylindrical body defining a longitudinal axis and having a first end and a second end, said body open at said first end and closed at said second end;
   at least one longitudinally extending, thin breakable-seal web formed on the exterior surface of said body, said at least one breakable-seal web defining a radially inwardly extending, hollow cavity for storing a lubricant; and
   a flaccid pouch harness comprising an annular retaining ring attached to said body adjacent said first end.

2. A male condom according to claim 1 further comprising at least one application handle attached to said retaining ring.

3. A male condom according to claim 2 wherein said at least one application handle extends radially and depends generally outwardly from the exterior surface of said retaining ring.

4. A male condom according to claim 2 wherein said at least one application handle extends longitudinally and depends generally rearwardly from the exterior surface of said retaining ring.

5. A male condom according to claim 2 wherein said at least one application handle is formed in a closed loop.

6. A male condom according to claim 2 wherein said at least one application handle comprises a plurality of circumferentially spaced application handles.

7. A male condom according to claim 6 wherein said plurality of application handles comprises a pair of diametrically opposed application handles.

8. A male condom according to claim 7 wherein said plurality of application handles further comprises a third application handle positioned medially between said pair of diametrically opposed application handles.

9. A male condom according to claim 6 wherein said plurality of application handles comprises a first pair of diametrically opposed application handles and a second pair of diametrically opposed application handles positioned generally perpendicular to said first pair of diametrically opposed application handles.

10. A male condom according to claim 1 wherein said flaccid pouch harness further comprises at least one longitudinally extending retaining band attached to said retaining ring and depending generally rearwardly therefrom, said at least one retaining band having a first end and a second end.

11. A male condom according to claim 10 wherein said first end of said at least one retaining band and said second end of said at least one retaining band are attached to said retaining ring at diametrically opposed positions.

12. A male condom according to claim 10 wherein said at least one retaining band is formed in a closed loop.

13. A male condom according to claim 12 wherein said at least one retaining band comprises a pair of retaining bands, each of said retaining bands attached to said retaining ring on one side and to the other of said pair of retaining bands on the other side.

14. A male condom according to claim 1 wherein said at least one breakable-seal web comprises a plurality of circumferentially spaced, longitudinally extending, breakable-seal webs.

15. A male condom according to claim 14 wherein said plurality of breakable-seal webs comprises a pair of diametrically opposed, breakable-seal webs.

16. A male condom according to claim 14 wherein said plurality of breakable-seal webs comprises a first pair of diametrically opposed, breakable-seal webs and a second pair of diametrically opposed, breakable-seal webs positioned generally perpendicular to said first pair of breakable-seal webs.

17. A male condom according to claim 1 further comprising a laterally extending, thin breakable-seal entrance shield positioned adjacent said first end of said body for temporarily closing said body at said first end, said entrance shield comprising a generally cylindrical flap having a plurality of radially extending perforations formed therein.

18. A male condom for preventing unwanted pregnancy and protecting against communicable diseases transmitted by the exchange of bodily fluids, said male condom comprising
   a flaccid pouch comprising an elongate, hollow, generally cylindrical body defining a longitudinal axis and having a first end and a second end, said body open at said first end and closed at said second end; and
   at least one longitudinally extending, thin breakable-seal web formed on the exterior surface of said body, said at least one breakable-seal web defining a hollow cavity for storing a lubricant;
   wherein said breakable-seal web opens longitudinally along its entire length to release the lubricant.

19. A male condom for preventing unwanted pregnancy and protecting against communicable diseases transmitted by the exchange of bodily fluids, said male condom comprising
   a flaccid pouch comprising an elongate, hollow, generally cylindrical body defining a longitudinal axis and having a first end and a second end, said body open at said first end and closed at said second end; and at least one longitudinally extending, thin breakable-seal web formed on the exterior surface of said body, said at least one breakable-seal web defining a hollow cavity for storing a lubricant;

wherein the diameter of said body of said flaccid pouch is less than the diameter of a form-fitting male condom and expands to a diameter that is greater than the diameter of a form-fitting male condom when said at least one breakable-seal web is broken; and wherein said breakable-seal web opens longitudinally along its entire length to release the lubricant.

\* \* \* \* \*